(12) United States Patent
Carlyon

(10) Patent No.: US 9,408,971 B2
(45) Date of Patent: Aug. 9, 2016

(54) SELF-CAPPING SYRINGE ASSEMBLY WITH ONE-WAY VALVE

(75) Inventor: James L. Carlyon, Farmington, MO (US)

(73) Assignee: Covidien LP, Mansfield, MA (US)

(*) Notice: Subject to any disclaimer, the term of this patent is extended or adjusted under 35 U.S.C. 154(b) by 893 days.

(21) Appl. No.: 12/412,652

(22) Filed: Mar. 27, 2009

(65) Prior Publication Data

US 2009/0247961 A1  Oct. 1, 2009

Related U.S. Application Data

(60) Provisional application No. 61/040,929, filed on Mar. 31, 2008.

(51) Int. Cl.
*A61M 5/28* (2006.01)
*A61M 5/31* (2006.01)

(52) U.S. Cl.
CPC ............ *A61M 5/28* (2013.01); *A61M 5/3134* (2013.01); *A61M 2005/3128* (2013.01)

(58) Field of Classification Search
CPC .......... A61M 2005/3128; A61M 5/28; A61M 5/3134
USPC .......................... 604/533, 218, 256, 192, 247
See application file for complete search history.

(56) References Cited

U.S. PATENT DOCUMENTS

| | | | | |
|---|---|---|---|---|
| 3,570,484 A | * | 3/1971 | Steer et al. | 604/249 |
| 4,722,725 A | * | 2/1988 | Sawyer et al. | 604/27 |
| 5,135,512 A | | 8/1992 | Mazurik et al. | |
| 5,453,097 A | * | 9/1995 | Paradis | 604/247 |
| 5,735,825 A | * | 4/1998 | Stevens et al. | 604/218 |
| 5,807,345 A | * | 9/1998 | Grabenkort | 604/199 |
| 5,899,887 A | * | 5/1999 | Liu | 604/195 |
| 2003/0199812 A1 | * | 10/2003 | Rosenberg | 604/47 |
| 2006/0111667 A1 | * | 5/2006 | Matsuura | A61M 5/3145 604/93.01 |
| 2006/0189932 A1 | * | 8/2006 | Yang et al. | 604/110 |
| 2009/0030401 A1 | * | 1/2009 | Phillips | 604/533 |
| 2009/0099552 A1 | * | 4/2009 | Levy et al. | 604/533 |

FOREIGN PATENT DOCUMENTS

| | | |
|---|---|---|
| EP | 0 325 049 | 7/1989 |
| WO | WO 03/051434 | 6/2003 |
| WO | WO 2006/136769 | 12/2006 |

OTHER PUBLICATIONS

European Patent Search Report dated Oct. 18, 2011 for European Patent Appln. No. EP 11 00 7214.

* cited by examiner

*Primary Examiner* — Aarti B Berdichevsky
*Assistant Examiner* — Brandy S Lee

(57) ABSTRACT

A syringe assembly is disclosed which includes a syringe body defining a fluid reservoir, a plunger assembly including a plunger rod and a sealing member supported on the plunger rod, and a luer cap releasably secured to a distal end of the syringe body. The luer cap includes a luer-type connector member and a fluid outlet. A one way valve is supported within the fluid outlet of the luer cap to prevent flow from the fluid outlet back into the fluid reservoir of the syringe body.

10 Claims, 4 Drawing Sheets

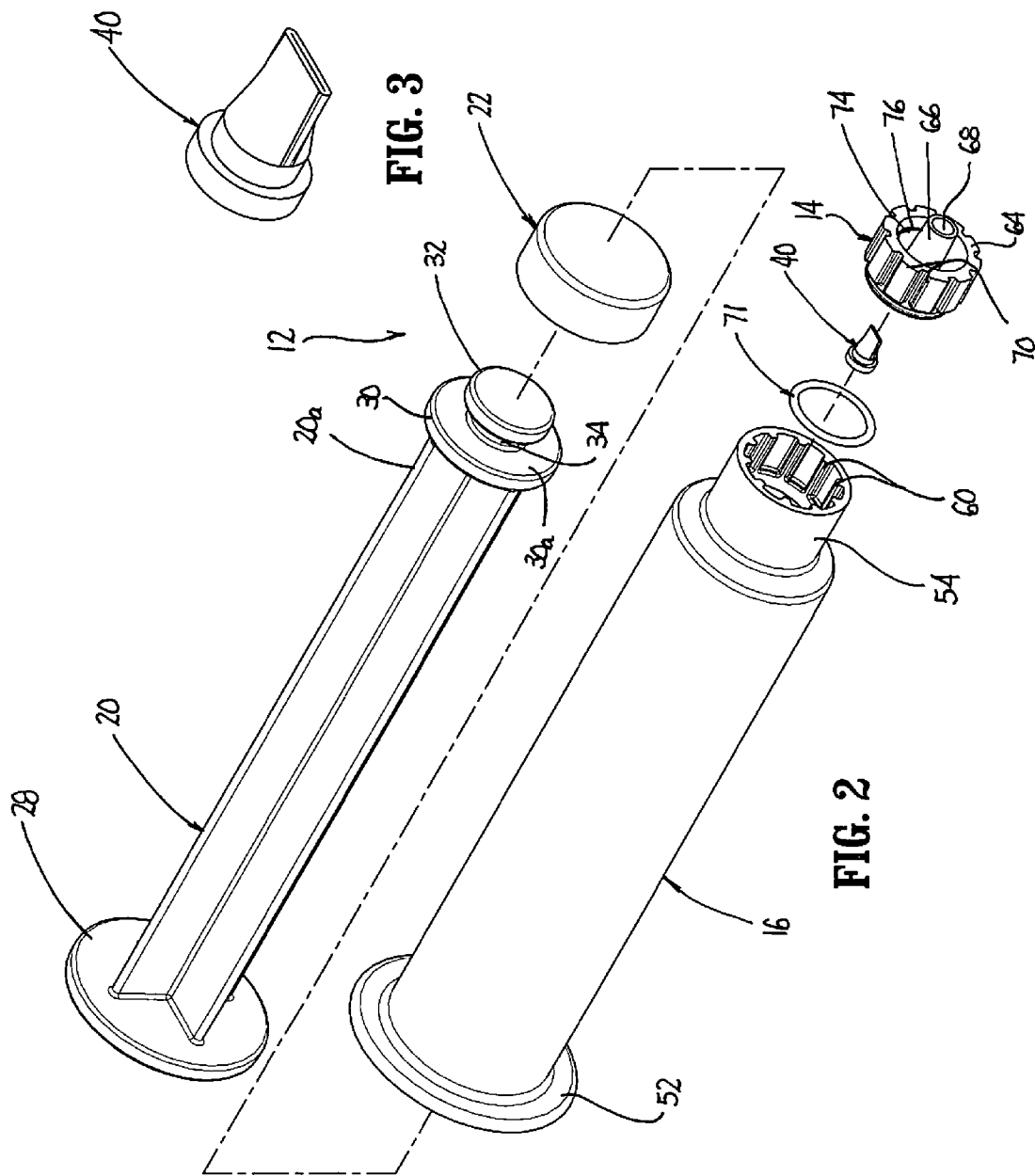

SELF-CAPPING SYRINGE ASSEMBLY WITH ONE-WAY VALVE

CROSS REFERENCE TO RELATED APPLICATION

This patent application claims priority to U.S. Provisional Application Ser. No. 61/040,929, filed Mar. 31, 2008, which is incorporated herein in its entirety by reference.

BACKGROUND

1. Technical Field

The present disclosure relates to syringes and, more particularly, to a syringe having a luer cap including anti-reflux capabilities for transfer to an indwelling catheter.

2. Background of Related Art

Intravenous or I.V. catheters which are inserted into a patient's vasculature, e.g., vein, to facilitate a variety of different medical procedures, including blood withdrawal, medication delivery, dialysis, etc., over an extended period of time are well known in the art. Such I.V. catheters minimize the pain and discomfort to a patient associated with multiple needle injections which may be required during a hospital stay.

One problem associated with I.V. catheters is that I.V. catheters are susceptible to clotting and may also lead to infection. More particularly, if blood stagnates within the catheter, the blood will eventually clot and occlude the catheter lumen. Further, stagnant blood provides a food source for planktonic bacteria which may form a biofilm and cause infection.

To overcome these problems, systems have been developed for flushing I.V. catheters after fluid has been injected into or removed from the catheter. In one such system, a syringe having a luer connector which is pre-filled with a fluid or lock solution, e.g., saline or heparin, is connected to the I.V. catheter and fluid is dispensed from the syringe to flush any medicament, blood or other fluid from the catheter.

Typically, an I.V. catheter includes a valve structure connected to a proximal end of the catheter which imparts either neutral or positive (distal direction) displacement upon the fluid in the catheter when a syringe is detached from the valve structure. One problem associated with known valve structures is that repeated access increases the potential for introducing bacteria and other microorganisms into the catheter leading to infection. Furthermore, at times, these valve structures don't eliminate the existence of reflux, i.e., fluid or blood flow back into the distal end of the catheter. As discussed above, reflux may result in clotting of the catheter or infection and is undesirable.

Accordingly, a continuing need exists in the medical arts for a syringe type flush system which can be easily connected to an I.V. catheter assembly, operated in a conventional manner and used as a means for capping or sealing off the proximal end of the catheter without causing reflux, thus obviating the need for reusable valve structures.

SUMMARY

A self-capping syringe assembly with a one way valve is disclosed which includes a syringe body defining a fluid reservoir and an outlet opening, a plunger assembly including a plunger rod and a sealing member supported on the plunger rod and a luer cap releasably secured to a distal end of the syringe body for providing a means to seal an inlet end of an I.V. catheter. The luer cap includes a luer-type connector member and defines a fluid outlet positioned to communicate with the outlet opening of the syringe body. A one-way valve is positioned within the fluid outlet to allow fluid to flow from the outlet opening through the fluid outlet but to prevent flow from the fluid outlet back into the outlet opening.

In one embodiment, the syringe body includes a hub portion defining a recess dimensioned to receive the luer cap. The luer cap can be frictionally retained in the recess of the hub portion.

In one embodiment, an outer surface of the luer cap includes a first plurality of spaced longitudinally extending ribs and the inner surface of the hub portion of the syringe body includes a second plurality of spaced longitudinally extending ribs which define channels dimensioned to slidably receive the first plurality of spaced longitudinally extending ribs to frictionally retain the luer cap within the hub portion of the syringe body.

In one embodiment, the one way valve is a duck-bill type one way valve. The luer cap can include an outer cylindrical body portion and an inner tapered body portion wherein the inner tapered body portion defines the fluid outlet. The outer cylindrical body and the inner tapered body portion can be spaced to define an annular channel wherein a helical-type coupling member is defined within the annular channel.

A luer cap is also disclosed which includes an outer cylindrical body portion configured and dimensioned to frictionally engage a syringe body, an inner body portion spaced from the outer body portion defining a fluid outlet, and a one way valve supported within the fluid outlet. A helical-type coupling member can be formed on the outer cylindrical body portion.

The coupling member can be positioned within an annular channel defined between the outer cylindrical body portion and the inner body portion. The inner body portion can have a tapered outer surface.

BRIEF DESCRIPTION OF THE DRAWINGS

Various embodiments of the presently disclosed self-capping syringe assembly with one way valve are disclosed herein with reference to the drawings, wherein:

FIG. 2 is an exploded, side perspective view of the self-capping syringe assembly with one way valve shown in FIG. 1;

FIG. 3 is an enlarged side perspective view of the one-way valve of the self-capping syringe assembly with one way valve shown in FIG. 2;

DETAILED DESCRIPTION OF EMBODIMENTS

Figure 1:
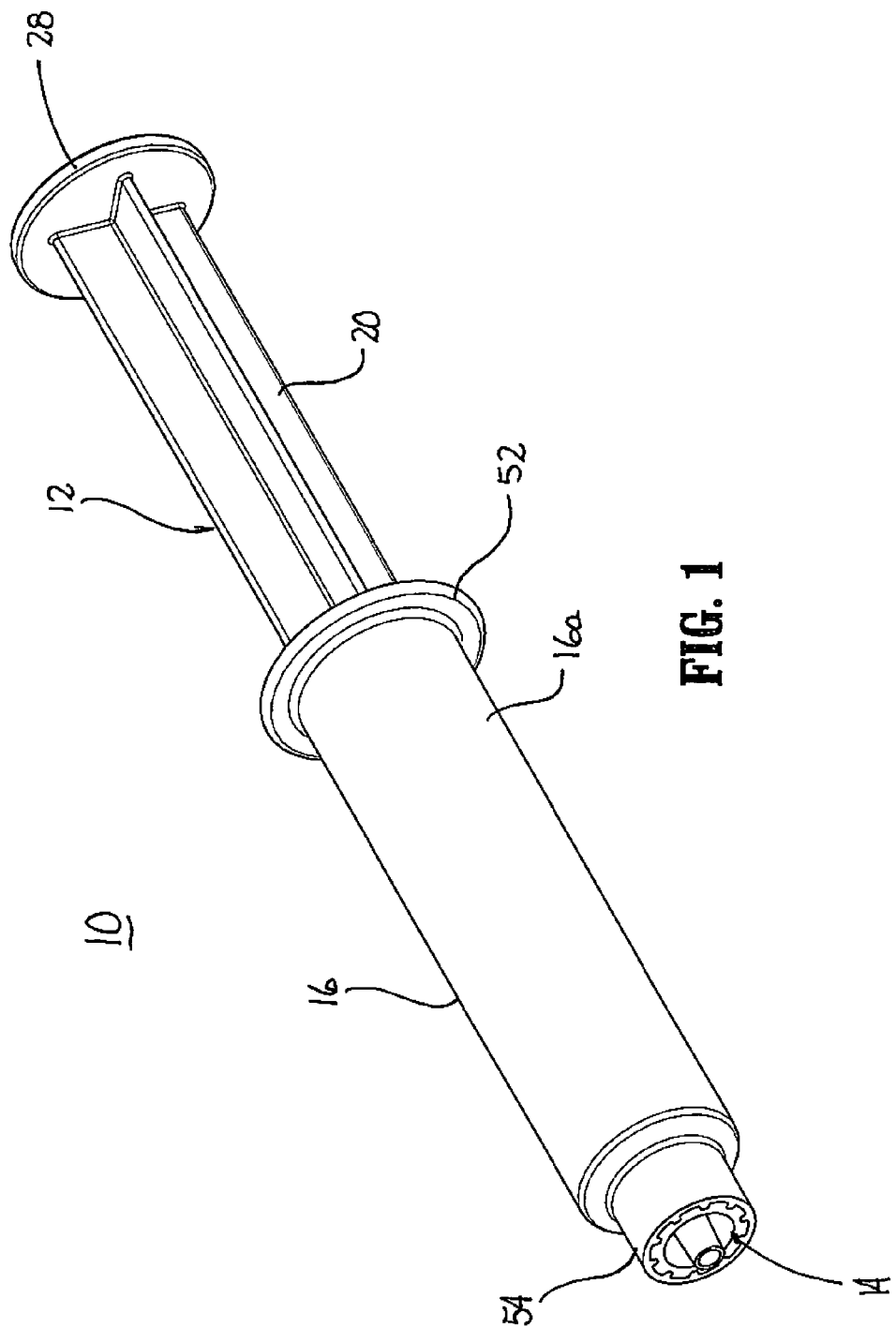
FIG. 1 is a side perspective view of one embodiment of the presently disclosed self-capping syringe assembly with one way valve.

Embodiments of the presently disclosed self-capping syringe assembly with one way valve and its method of use will now be described in detail with reference to the drawings wherein like reference numerals designate identical or corresponding elements in each of the several views. In this description, the term proximal is generally used to indicate the relative nearness of a referenced item to a user of the device and the term distal is used to indicate the relative remoteness of a referenced item to a user of the device.

Figure 4:
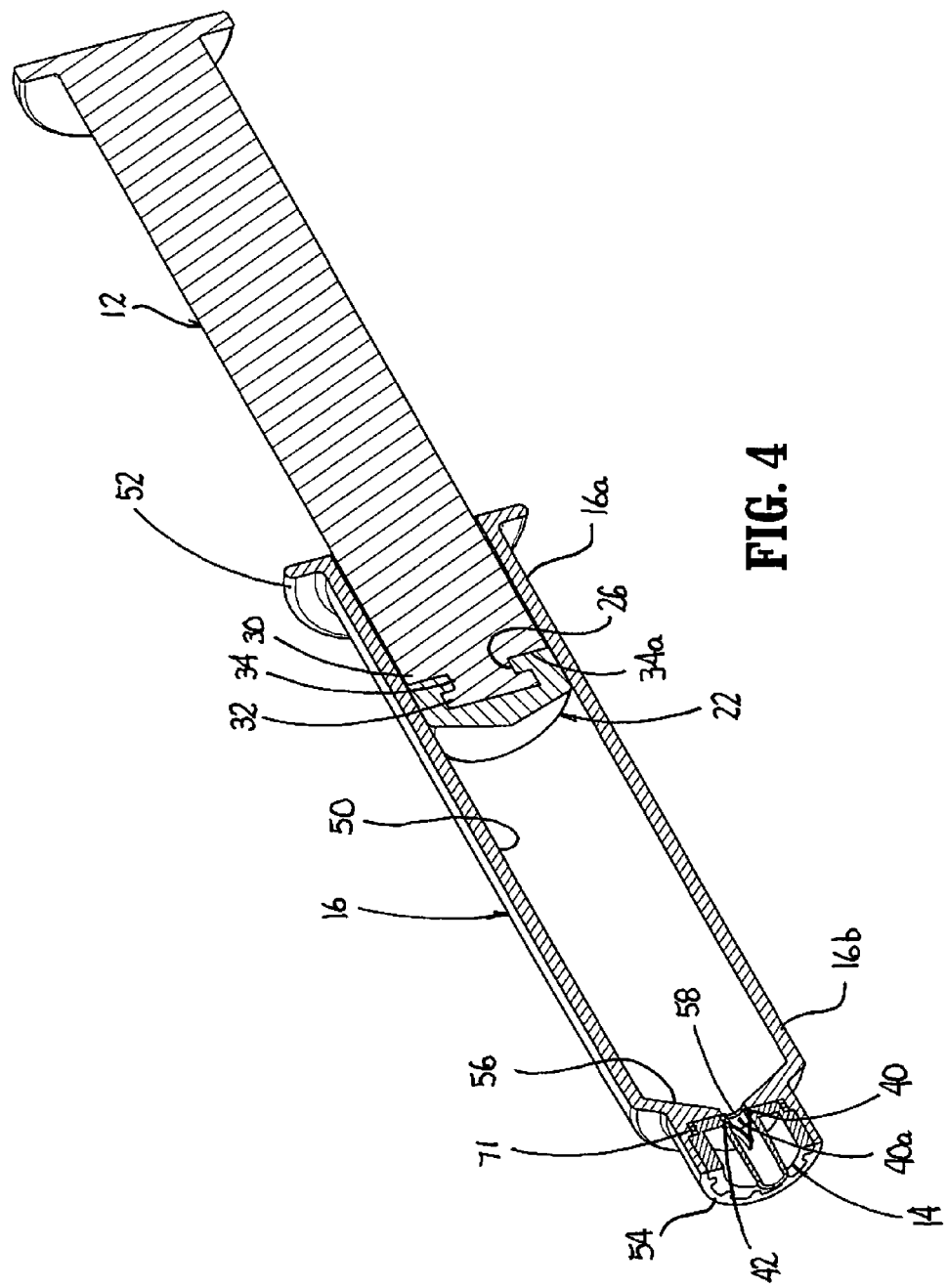
FIG. 4 is a side cross-sectional view of the self-capping syringe assembly with one way valve shown in FIG. 1 with the plunger in a retracted position prior to operation of the system.

FIGS. 1-4 illustrate one embodiment of the presently disclosed self-capping syringe assembly with one way valve shown generally as 10. Briefly, syringe assembly 10 includes a plunger assembly 12, a luer cap 14, and a syringe body 16. Plunger assembly 12 includes a plunger rod 20 and a sealing member 22. Sealing member 22 is supported on a distal end 20a of plunger rod 20 and defines a stepped throughbore 26 (FIG. 4). A proximal end of plunger rod 20 has a finger engagement member 28. Distal end 20a of plunger rod 20 includes a large diameter transverse disc portion 30, a small diameter disc portion 32 and an intermediate step portion 34 connecting disc portions 30 and 32. When sealing member 22 is supported on plunger rod 20, a distal face 30a (FIG. 2) of disc portion 30 abuts a proximal face 22a of sealing member 22 such that small diameter disc portion 32 and intermediate step portion 34 are positioned within stepped throughbore 26 of sealing member 22. Sealing member 22 can be formed from an elastomeric material, e.g., rubber, neoprene, etc. and is deformable to receive distal end 20a of plunger rod 20.

Referring to FIGS. 2 and 4, syringe body 16 defines a fluid reservoir 24 (FIG. 4) which is dimensioned to slidably receive plunger assembly 12 such that sealing member 22 slidably engages an inner wall 50 of syringe body 16. A proximal open end 16a of syringe body 16 includes a gripping flange 52 and a distal end 16b of syringe body 16 includes a cylindrical hub portion 54. A wall 56 (FIG. 4) formed at the distal end of reservoir 24 defines an outlet opening 58 which communicates with reservoir 24. Cylindrical hub portion 54 defines cavity 54a (FIG. 6) dimensioned to releasably receive luer cap 14.

Figure 6:
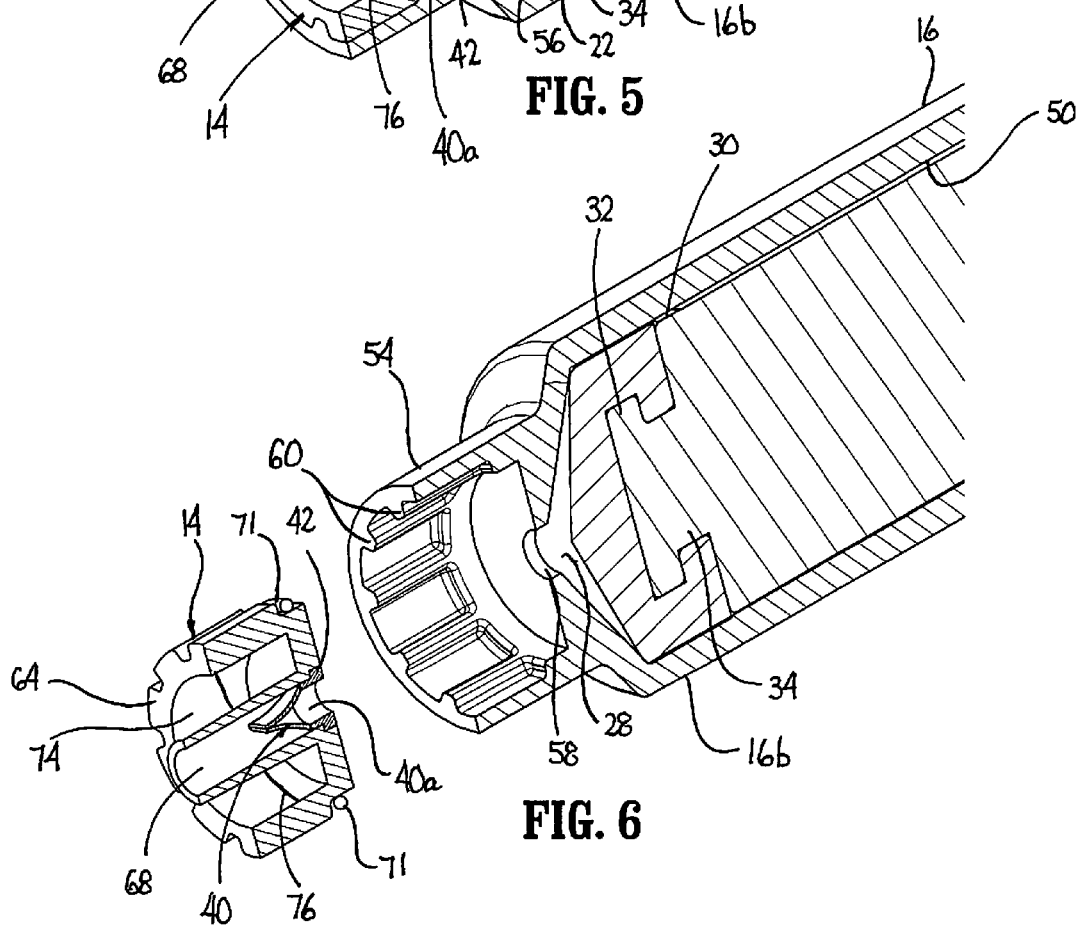
FIG. 6 is an enlarged side cross-sectional view of the distal end of the self-capping syringe assembly with one way valve shown in FIG. 5 with the plunger rod fully advanced and the luer cap disengaged from the hub of the syringe body.

Referring to FIGS. 2 and 6, a series of spaced longitudinally extending ribs 60 are positioned about an inner surface of hub portion 54. As will be discussed in further detail below, ribs 60 are configured to releasably retain luer cap 14 within hub portion 54 of syringe body 16.

Luer cap 14 includes an outer cylindrical body portion 64 and an inner tapered body portion 66 which defines a fluid outlet or channel 68. Fluid outlet 68 is positioned to be in fluid communication with outlet opening 58 of syringe body 16 such that outlet 68 communicates with reservoir 24. The outer surface of outer cylindrical body portion 64 includes a plurality of spaced longitudinally extending ribs 70. Each of ribs 70 is dimensioned to be frictionally retained between a pair of ribs 60 of hub portion 54 to frictionally retain luer cap 14 within cavity 54a of hub portion 54. Ribs 60 and 70 prevent relative rotation between hub portion 54 and luer cap 14 during securement of syringe assembly 10 to an I.V. or indwelling catheter assembly (not shown). A sealing member 71, e.g., an elastic O-ring, can be positioned between an outer surface of luer cap 14 and an inner surface of hub portion 54 to prevent fluid leakage about luer cap 14. As illustrated, the engaging surfaces of ribs 60 and 70 can be roughened, ribbed, knurled or the like to improve retention of luer cap 14 within cavity 54a of hub portion 54. It is envisioned that luer cap 14 can be retained within hub portion 54 using other known means of retention, e.g., detents, frangible structure, etc Referring to FIGS. 2-4, a one-way valve 40 is supported within fluid outlet 68 of luer cap 14. One-way valve 40 is configured to allow fluid to flow from fluid reservoir 24 through outlet opening 58 and through fluid outlet 68 but to prevent fluid from flowing from fluid outlet 68 back into reservoir 24. Valve 40 can be dimensioned such that when luer cap 14 is retained within cavity 54a of hub portion 54, the proximal face of body 42 of valve 40 contacts hub portion 54 on a surface that surrounds outlet opening 58 to prevent the release of pressure around luer cap 14. One-way valve 40 is illustrated as a duck-bill type check valve. Check valve 40 is formed of a resilient material which defines an opening 40a which is normally closed but will open when the pressure within body 42 of valve 40 exceeds a predetermined minimum pressure. This will occur when plunger assembly 12 is moved towards the advanced position. It is envisioned that a variety of different types of one-way valves can be used including spring-loaded valves, ball valves, valves having resilient slits, etc.

Outer cylindrical body portion 64 and inner tapered body portion 66 define an annular channel 74 (FIG. 6). Body portion 64 includes an internal thread 76 (FIG. 2) which forms a helical-type coupling member. Coupling member 76 is configured to releasably engage a helical coupling member of an I.V. or indwelling catheter assembly (not shown) to secure syringe assembly 10 to the catheter assembly.

Referring to FIG. 4, when syringe assembly 10 is used to flush an indwelling catheter (not shown), luer cap 14 is secured to the indwelling catheter via coupling member 76. Prior to actuation of syringe assembly 10, plunger assembly 12 is in a retracted position with sealing member 22 spaced from distal wall 56 of syringe body 18.

Figure 5:
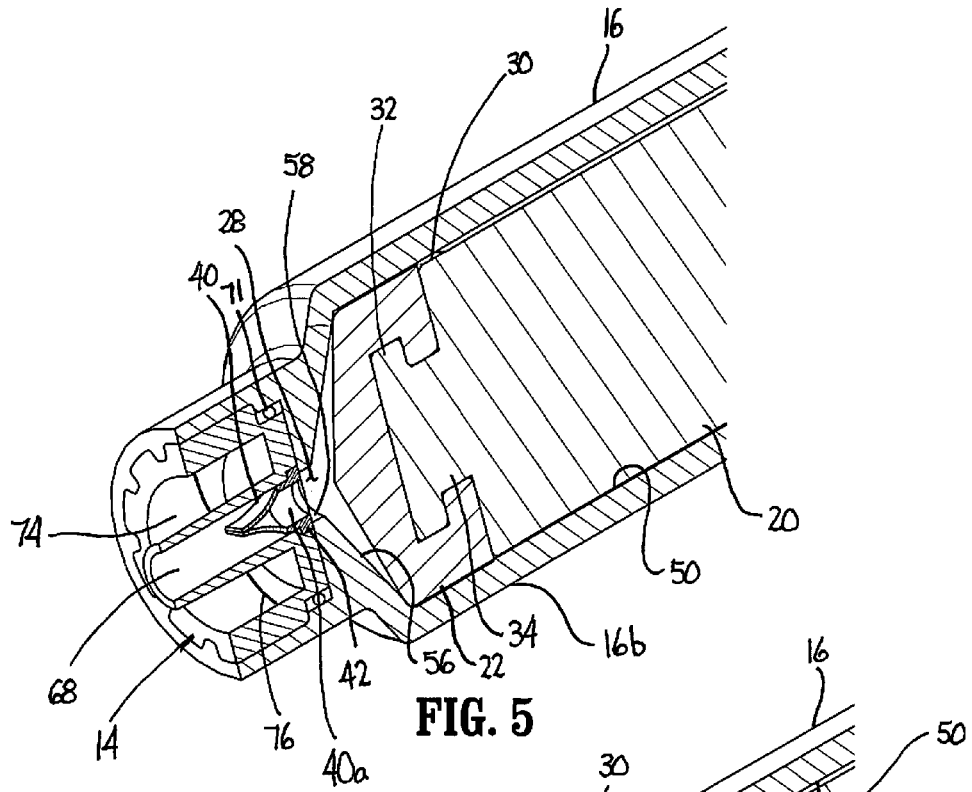
FIG. 5 is an enlarged side, cross-sectional view of the distal end of the self-capping syringe assembly with one way valve shown in FIG. 4 with the plunger rod moved to the advanced position.

Referring to FIG. 5, when plunger assembly 12 is moved from the retracted position to the advanced position, fluid is forced from reservoir 24, through outlet opening 58 into fluid outlet 68 and into one-way valve 40. When the pressure in fluid outlet 68 exceeds a predetermined minimum, one-way valve 40 opens to allow fluid to flow from fluid outlet 68 into an indwelling catheter. It is noted that the entire contents of fluid reservoir 24 need not be dispensed from syringe assembly 10, i.e., one way valve 40 will function to seal fluid outlet 68 after only a portion of fluid reservoir 24 is dispensed. Thus, the plunger assembly does not have to be moved to its fully advanced position to effect operation of one way valve 40.

Referring to FIG. 6, after the desired amount of fluid has been dispensed from syringe assembly 10, syringe body 16 can be separated from luer cap 14 and the indwelling catheter (not shown) by holding one of luer cap 14 and syringe body 16 stationary and manually separating the components. When separated, luer cap 14 remains connected to an inlet end of the indwelling catheter to seal the inlet end of the indwelling catheter and prevent reflux from occurring.

It will be understood that various modifications may be made to the embodiments disclosed herein. For example, a variety of different techniques or devices can be used to retain the luer cap within the hub portion of the syringe body including frangible couplings, detents, interlocking components, etc. Although syringe assembly 10 has been disclosed as being suitable for use with indwelling catheters, syringe assembly 10 may also be used in other medical applications. Therefore, the above description should not be construed as limiting, but merely as exemplifications of preferred embodiments. Those skilled in the art will envision other modifications within the scope and spirit of the claims appended hereto.

What is claimed is:

1. A self-capping syringe assembly comprising:
  a syringe body defining a fluid reservoir and an outlet opening;
  a plunger assembly including a plunger rod and a sealing member supported on a distal end of the plunger rod;

a luer cap including retention structure to releasably secure the luer cap to a distal end of the syringe body, the luer cap including a luer-type connector member adapted to engage an I.V. catheter assembly and defining a fluid outlet positioned to communicate with the outlet opening of the syringe body; and a one-way valve positioned within the fluid outlet of the luer cap, the one way valve being configured to allow fluid to flow from the outlet opening through the fluid outlet but to prevent fluid flow from the fluid outlet back into the outlet opening.

2. The self-capping syringe assembly with one way valve according to claim 1, wherein the syringe body includes a hub portion defining a recess dimensioned to receive the luer cap.

3. The syringe assembly according to claim 2, wherein the luer cap is frictionally retained in the recess of the hub portion by the retention structure.

4. The syringe assembly according to claim 3, wherein the retention structure is formed on an outer surface of the luer cap and includes a first plurality of spaced longitudinally extending ribs.

5. The syringe assembly according to claim 4, wherein the inner surface of the hub portion of the syringe body includes a second plurality of spaced longitudinally extending ribs which define channels dimensioned to slidably receive the first plurality of spaced longitudinally extending ribs to frictionally retain the luer cap within the hub portion of the syringe body.

6. The syringe assembly according to claim 1, wherein the one way valve is a duck-bill type one way valve.

7. The syringe assembly according to claim 1, wherein the luer cap includes an outer cylindrical body portion and an inner tapered body portion.

8. The syringe assembly according to claim 7, wherein the inner tapered body portion defines the fluid outlet.

9. The syringe assembly according to claim 8, wherein the outer cylindrical body and the inner tapered body portion are spaced to define an annular channel.

10. The syringe assembly according to claim 9, further including a helical-type coupling member defined within the annular channel adapted to engage an I.V. catheter assembly.

* * * * *